United States Patent [19]

Keyes et al.

[11] Patent Number: 5,380,309
[45] Date of Patent: Jan. 10, 1995

[54] FLUSHABLE OSTOMY POUCH WITH MECHANICAL COUPLING

[75] Inventors: Denis E. Keyes, Rocky Hill; Kenneth Johnsen, Piscataway, both of N.J.

[73] Assignee: E. R. Squibb & Sons, Inc., Princeton, N.J.

[21] Appl. No.: 257,499

[22] Filed: Jun. 9, 1994

Related U.S. Application Data

[63] Continuation-in-part of Ser. No. 14,953, Feb. 8, 1994, abandoned.

[51] Int. Cl.⁶ .................................................. A61F 5/44
[52] U.S. Cl. .................................. 604/338; 604/332; 604/342
[58] Field of Search .................................. 604/332–345

[56] References Cited

U.S. PATENT DOCUMENTS

| | | | |
|---|---|---|---|
| 2,721,553 | 10/1955 | Perry | 604/342 |
| 4,460,363 | 7/1984 | Steer et al. | 604/339 |
| 4,762,738 | 8/1988 | Keyes et al. | 604/332 |
| 5,009,648 | 4/1991 | Aronoff et al. | 604/332 |
| 5,015,244 | 5/1991 | Cross | 604/338 |

FOREIGN PATENT DOCUMENTS 2083762  3/1982  United Kingdom ............... 604/332

*Primary Examiner*—Randall L. Green
*Assistant Examiner*—Rob Clarke
*Attorney, Agent, or Firm*—Stuart E. Krieger

[57] ABSTRACT

The ostomy pouch has a coupling member that can be removed from the pouch envelope to permit flush disposal of the envelope without the coupling member. Flushability of the pouch is further enhanced by forming the pouch with converging side walls. Thus when the pouch is deposited in a toilet bottom end first in a carrier sleeve, the pouch can flow in streamlined fashion through the passages of a toilet and any sewer pipe or septic line connected to the toilet. Depending upon the flush capacity of the toilet and the flow rate of water through the toilet and sewer line, the ostomy pouch can be deposited in the toilet without a carrier sleeve.

17 Claims, 4 Drawing Sheets

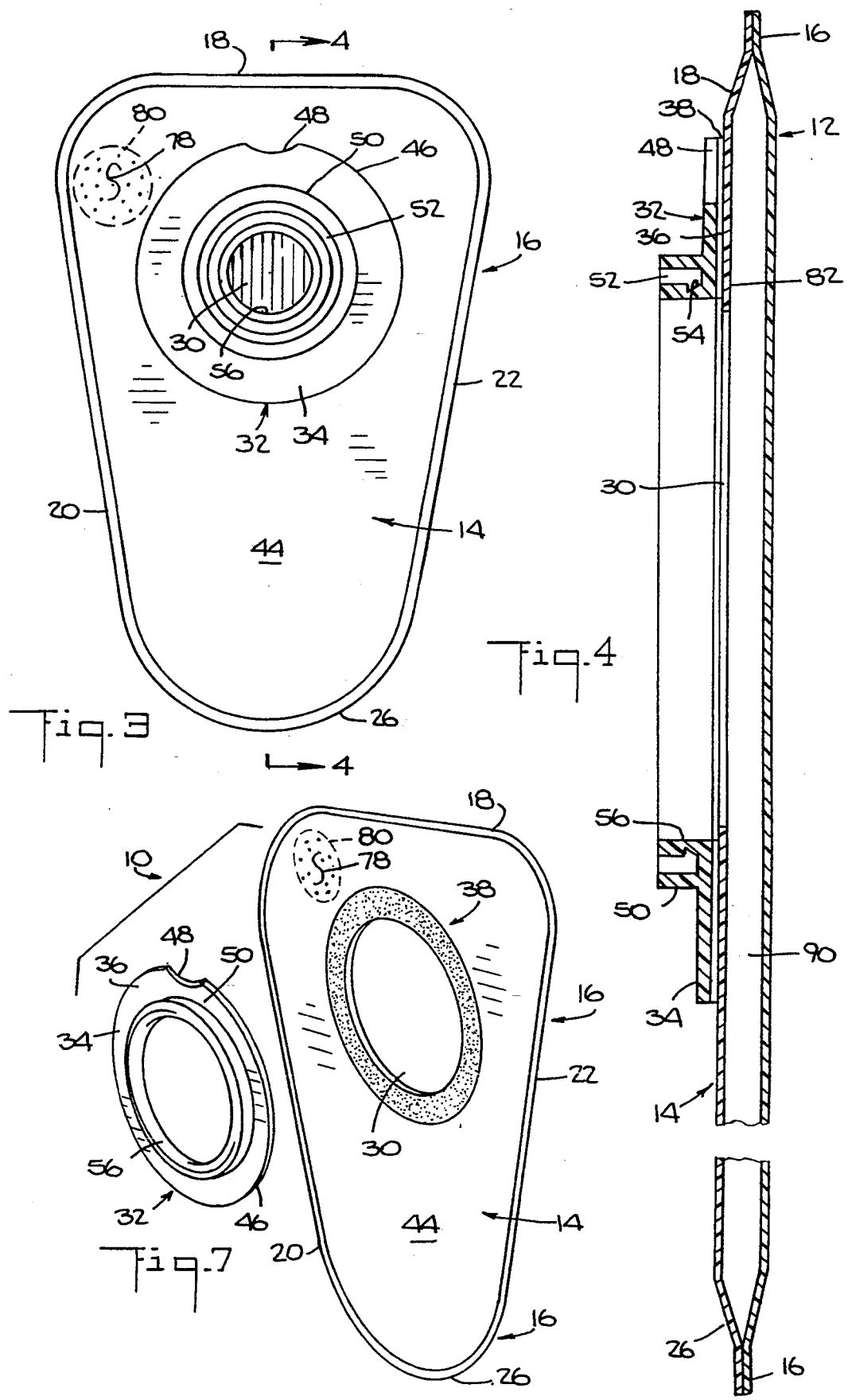

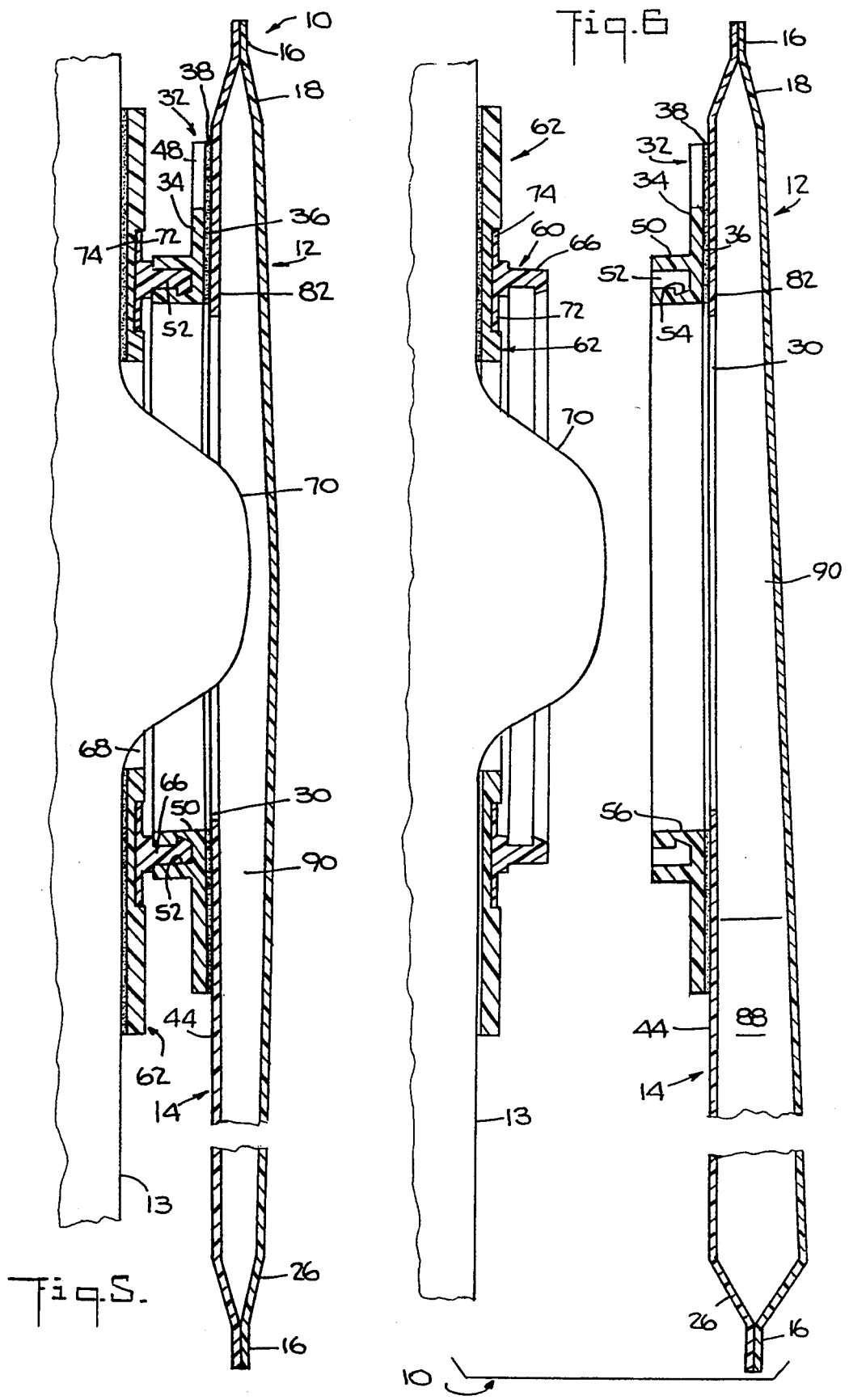

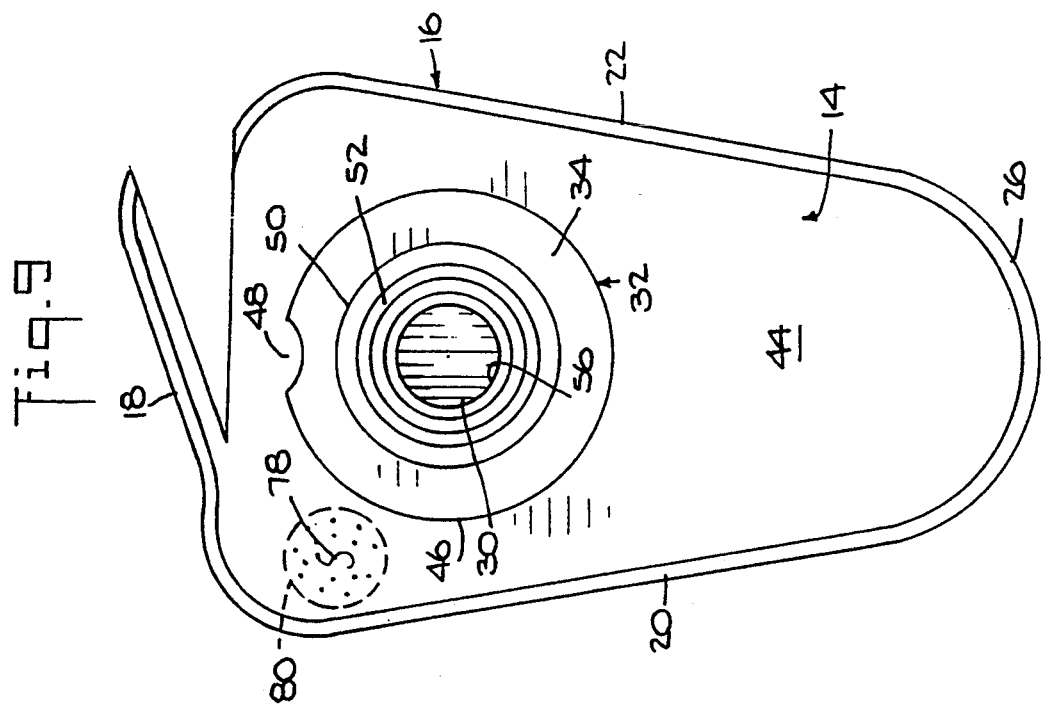
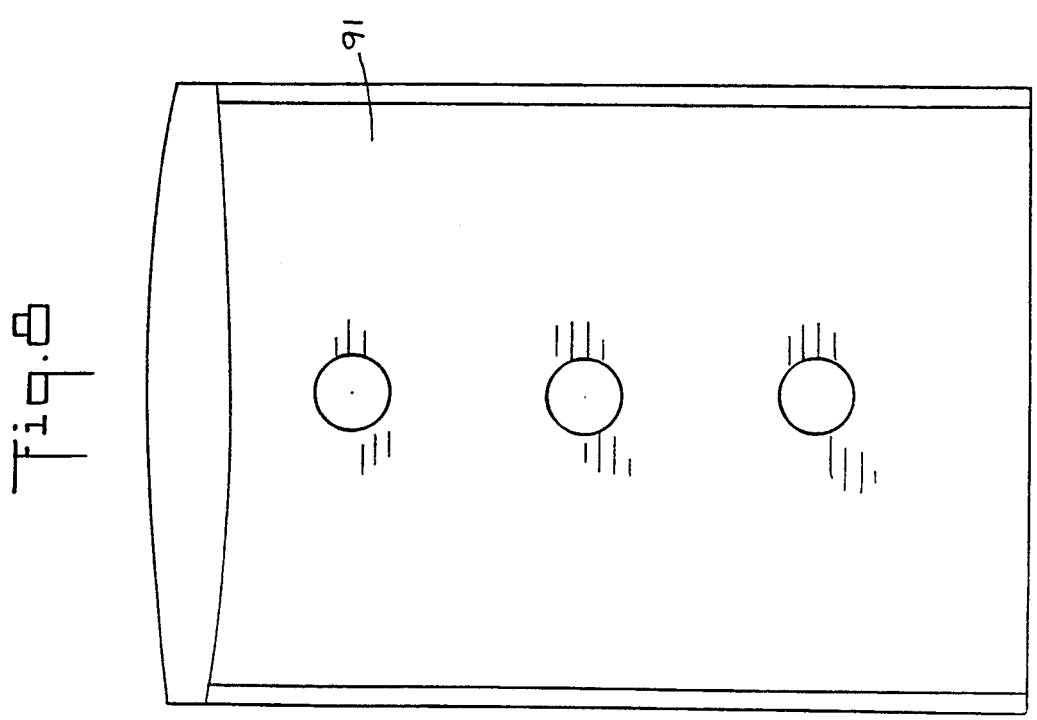

FLUSHABLE OSTOMY POUCH WITH MECHANICAL COUPLING

This is a continuation-in-part of application Ser. No. 08/014,953, filed Feb. 8, 1994, now abandoned.

BACKGROUND OF THE INVENTION

This invention is directed to ostomy pouches and more particularly to a novel flushable ostomy pouch.

One of the problems associated with ostomy care is the disposal of the ostomy collection pouch after it has been used. If the used pouch is disposed of by flushing down a toilet, there is a risk that the pouch may become trapped in a toilet passage or sewer line, thereby causing plumbing problems. Thus some users empty the contents of the pouch into the toilet and then discard the pouch in the garbage.

Other users dispose of the used pouch and its contents in the garbage, which usually necessitates prewrapping of the pouch with paper and/or placement of the used pouch in a plastic bag prior to disposal. Regardless of which measures are taken to dispose of a used ostomy pouch, the process is generally unduly laborious and oftentimes discomforting.

Thus there has been an ongoing effort to develop an ostomy pouch that provides relatively trouble-free flushability down a toilet.

A major problem in flushing an ostomy pouch down a toilet is that the coupling or securing structure around the waste inlet opening of the ostomy pouch, such as shown in U.S. Pat. No. 4,372,308, can cause the pouch to become trapped in the flow passages of the toilet or in a connecting pipe or sewer line.

Efforts have thus been made to form ostomy pouches of materials that soften and become slimy or slippery when contacted with water to promote flowage in pipelines and flow passages.

While pouches that become slimy or slippery upon contact with water help minimize clogging and trapping problems associated with flush disposal of ostomy pouches, they can be discomforting if they become wet while being worn. Such pouches might discourage a user from engaging in swimming and other physical activity and would require protective covering while showering. Furthermore, such pouches may still cause clogging in toilets with relatively low volume flush capacity.

Another structure that facilitates flush disposal of ostomy pouches is that of U.S. Pat. No. 4,830,187, which shows a carrier sleeve or bag into which a pouch can be placed before flush disposal. The sleeve or bag forms a slimy or slippery layer when exposed to water, thereby sliding on surfaces that might otherwise cause snagging of the pouch. However, since the carrier sleeve conforms to the pouch during flushing, a pouch with a coupling that is not flexible enough to negotiate the flow passages in a toilet may still become trapped even with a slippery carrier sleeve.

It is thus desirable to provide an ostomy pouch that can be adapted to easily flush down a toilet, even a water-saver toilet, and which has an optimum height, width, and convergence angle to facilitate flush disposal.

OBJECTS AND SUMMARY OF THE INVENTION

Among the several objects of the invention may be noted the provision of a novel ostomy pouch, a novel ostomy pouch that can be disposed of by flushing down a water-saver toilet, a novel ostomy pouch with a detachable coupling member, a novel ostomy pouch with a detachable coupling member that can be separated from the pouch prior to disposal of the pouch, a novel ostomy pouch having a coupling member that can be separated from the pouch as a unit without damaging the pouch to facilitate flush disposal of the pouch, a novel ostomy pouch with a detachable coupling member that can be reused, a novel ostomy pouch which has a converging streamlined shape from top to bottom with an optimum angle of convergence, optimum width, and optimum height to facilitate flush disposal in a water-saver toilet, and a novel method for facilitating flush disposal of an ostomy pouch.

Other objects and features of the invention will be in part apparent and in part pointed out hereinafter.

In accordance with the invention, the flushable ostomy pouch includes an envelope formed of flexible plastic sheet material that defines a waste collection chamber for body waste that passes through a stoma. A waste inlet opening is formed in the envelope for passage of waste material from the stoma into the collection chamber. Coupling means are provided on the envelope around the waste inlet opening for positioning the waste inlet opening around the stoma. The coupling means can be formed of molded annular plastic to mechanically interengage with a complementary shaped coupling portion provided around the stoma.

The coupling member is detachably bonded to the envelope so as to permit removal from the envelope prior to flushing the pouch in a toilet. The bonding agent which joins the coupling member to the envelope has a predetermined bond strength that permits the coupling member to be peeled as a unit from the envelope. Thus the removal of the coupling means from the pouch facilitates flush disposal of the envelope even in a water-saver toilet which has less water volume flush capacity than a standard toilet, and minimizes the likelihood that the flushing of the pouch will result in trappage within the sewer line.

The removed coupling member can be discarded or reused on a replacement pouch.

In European wash down water closets, when the pouch is ready for disposal, the top portion of the pouch can be cut or otherwise ripped to permit evacuation of the contents of the collection chamber during the flush process.

Preferably the envelope has opposite side edges that converge from the top portion of the envelope to the bottom portion such that the envelope in plan view is substantially V-shaped. The top width, pouch height and convergence angle are of a predetermined magnitude to assure optimum flushability of the pouch. The pouch is placed bottom end down and can be deposited in a toilet with a sleeve or bag that becomes slippery upon contact with water.

The invention accordingly comprises the constructions and method hereinafter described, the scope of the invention being indicated in the claims.

DESCRIPTION OF THE DRAWINGS

In the accompanying drawings,

FIG. 3 is a plan view thereof;

FIG. 4 is a sectional view thereof, taken on the line 4—4 of FIG. 3;

FIG. 5 is a sectional view thereof, taken on the line 5—5 of FIG. 2;

FIG. 6 is a view similar to FIG. 5, showing the pouch, after use, uncoupled from the support flange;

FIG. 7 is a simplified perspective view thereof, after the coupling member and the pouch envelope have been separated; and FIG. 8 is a plan view of a carrier sleeve which can be used to flush an ostomy pouch in accordance with the present invention; and FIG. 9 is a plan view of an ostomy pouch in accordance with the present invention having a cut in its top portion.

Corresponding reference characters indicate corresponding parts throughout the several views of the drawings.

DETAILED DESCRIPTION OF THE INVENTION

Figure 1:
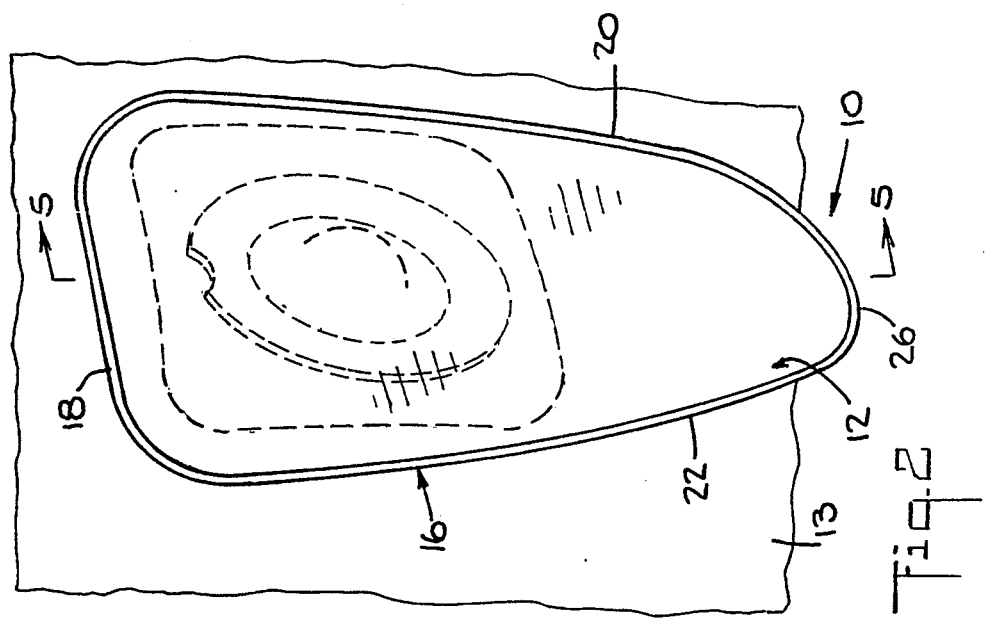
FIG. 1 is a simplified perspective view of an ostomy pouch incorporating one embodiment of the invention, prior to being coupled to a support flange provided around the stoma.
Figure 2:
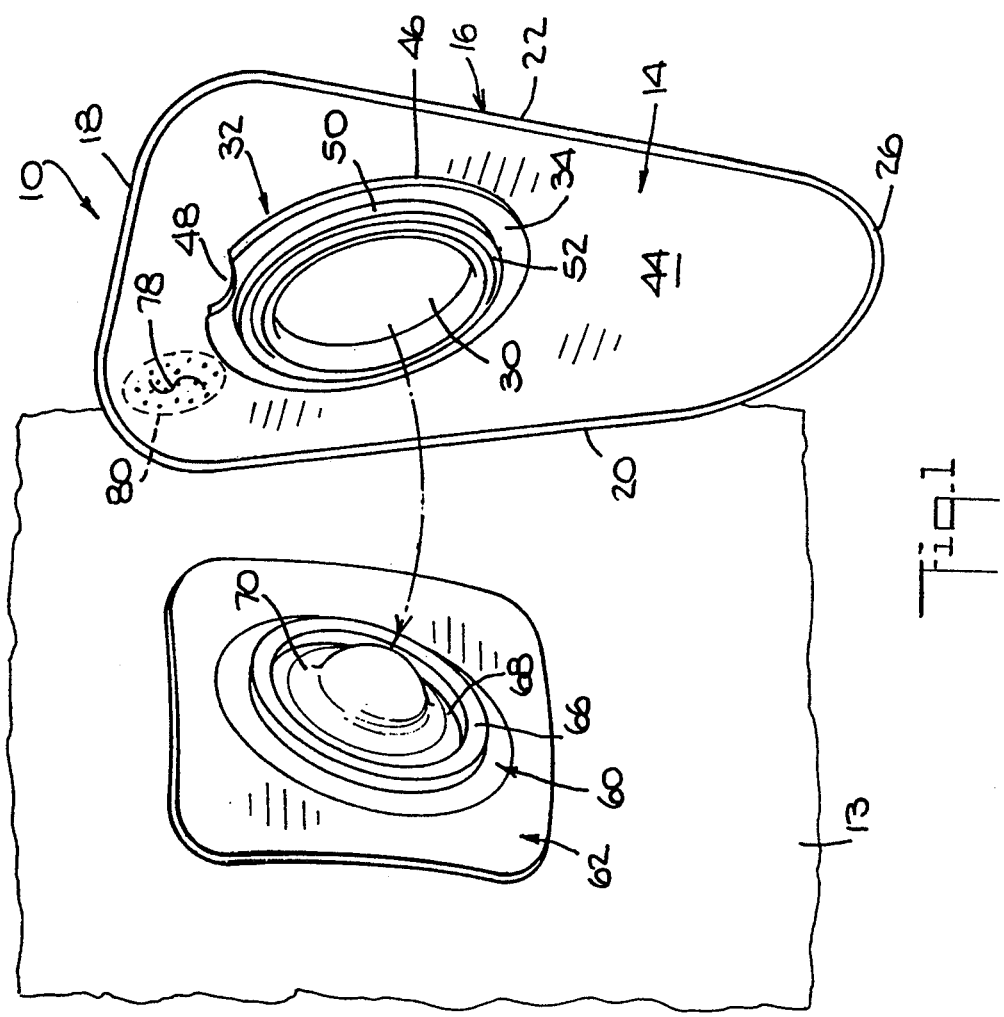
FIG. 2 is a simplified perspective view thereof after the pouch has been coupled to the support flange.

An ostomy pouch incorporating one embodiment of the invention is generally indicated by the reference number 10 in FIG. 1. The pouch 10 is formed of a suitable known thermoplastic material that is gas and water impermeable, flexible and expandable.

The pouch 10 includes a front wall 12 that faces away from the abdomen 13, and a rear wall 14 that confronts the abdomen 13, joined together by a peripheral thermoweld 16. The pouch 10 further includes a top portion 18 with rounded corners, and opposite side portions 20 and 22 that converge from the top portion 18 to a rounded bottom portion 26.

In a preferred embodiment of the pouch 10, the height of the pouch is approximately 7.750 inches, the maximum width of the top portion 18 at the rounded corners is approximately 5.125 inches, the bottom portion 26 has a radius of approximately 1.750 inches and the angle of convergence of the side portions 20 and 22 is approximately 15°. The walls 12 and 14 are approximately 17 to 45 microns thick.

A preferred size range for the pouch 10 is approximately 4.5 to 6 inches maximum width of the pouch, approximately 6 to 8 inches pouch height and a convergence angle of approximately 15° to 25°.

A waste inlet opening 30 is formed in the rear wall 14 nearer the top portion 18 of the pouch 10 than the bottom portion 26. The waste inlet opening 30 is bordered by a plastic coupling ring 32 (FIG. 7) having a base portion 34 and a bottom surface 36.

A contact adhesive 38 (FIG. 7) is provided on an outside surface 44 of the rear wall 14 in the form of a washer-shaped wafer approximately 0.010 to 0.015 inches thick, to bond the bottom surface 36 of the coupling ring 32 to the rear wall 14. Preferably the adhesive 38 is of a type that securely joins the coupling ring 32 to the rear wall 14 to prevent axial removal of the ring 32. However, the adhesive is selected to permit peeling of the coupling ring 32 from the rear wall 14 without damaging the rear wall.

A suitable adhesive 38 is a hydrocolloid adhesive such as Stomahesive ®, manufactured by Bristol-Myers Squibb Company. The adhesive wafer can be covered with a known silicone release paper (not shown) that is removed prior to installation of the coupling ring 32. Thus the coupling ring 32 can be easily positioned on the rear wall 14 by the user or the manufacturer.

The base portion 34 of the coupling ring 32 has a peripheral edge 46 with a generally concave touch indicator notch or recess 48. Preferably the coupling ring 32 is positioned such that the recess 48 is at the 12 o'clock position as shown in FIG. 4. The indicator notch 48 permits touch detection of an initial peel section of the coupling ring 32 at the area of the notch 48.

The coupling ring 32 further includes an annular rim 50 projecting away from the base portion 34. An annular engagement slot 52 formed in the rim 50 includes an undercut latch portion 54. An inner peripheral surface 56 of the rim 50 encircles the waste inlet opening 30 at the rear wall 14.

Referring to FIGS. 1, 5 and 6, the coupling ring 32 is adapted to interlock with a complementary shaped coupling ring 60 on a mounting plate 62 which is adapted to adhere to the abdominal wall 13 in any suitable known manner. A central opening 68 in the mounting plate 62, which aligns with the stoma 70, is surrounded by an annular latch projection 66 that interlocks in the engagement slot 52 of the coupling ring 32.

Preferably the coupling ring 60 and the mounting plate 62 are formed as a two-part structure wherein an annular base portion 72 of the coupling ring 60 is bonded to an annular channel 74 of the mounting plate 62.

An S-shaped gas evacuation slit 78 or other suitable gas evacuation outlet is formed in the rear wall portion 14 of the pouch 10 near the top and side edges 18 and 20, offset from the coupling ring 32. A generally circular deodorizing filter 80 of the type shown in U.S. Pat. No. 5,074,851, is provided at an inside surface 82 of the rear wall 14 in substantial alignment with the gas evacuation slit 78.

In using the ostomy pouch 10, the mounting plate 62 is first adhered to the abdominal wall 13 to align the central opening 68 with the stoma 70. The coupling ring 32 is installed on the rear wall 14 of the pouch 10 and engaged with the coupling ring 60 of the mounting plate 62 to interlock the latch projection 66 in the engagement slot 52 as shown in FIG. 5. A leak tight joint is thus established around the stoma 70 which also aligns with the waste inlet opening 30 of the ostomy pouch 10.

Waste material 88 (FIG. 6) that issues from the stoma 70 passes into a waste collection chamber 90 of the pouch 10. When an adequate amount of the waste material 88 accumulates in the collection chamber 90, the pouch 10 is ready for disposal.

To facilitate flush disposal of the used pouch, the welded wall portions 12 and 14 which constitute the envelope 12–14 of the pouch are separated from the coupling ring 32. Separation of the coupling ring 32 can be accomplished by peeling the rear wall 14 away from the base portion 36 of the coupling ring 32 while the coupling ring 32 is engaged with the coupling ring 60.

The adhesive bond between the coupling ring 32 and the tape 38 is of a predetermined strength that can be overcome by peeling without causing separation of the coupling rings 32 and 60. The peeling operation is initiated at the touch indicator notch 48 which is sized to permit finger engagement with the coupling ring 32.

Separation of the envelope 12-14 from the coupling ring 32 can also be accomplished by initially disengaging the coupling rings 32 and 60 and then peeling the ring 32 from the rear wall 14. Coupling disengagement is obtained by pressing a finger between the couplings 32 and 60 to release the pouch 10 from the mounting plate 62. The coupling ring 32 can then be peeled from the rear wall 14 while the ostomy pouch 10 is held at the top portion 18.

Once the coupling ring 32 is separated from the rear wall 14, the envelope 12-14, minus the coupling ring 32, can be flushed down a water-saver toilet, preferably with a carrier sleeve 91 (FIG. 8) of the type shown in U.S. Pat. No. 4,830,187. In European wash down water closets, the carrier sleeve 91 can be omitted. However, the top portion 18 is preferably cut or ripped (FIG. 9) to permit evacuation of confined waste during the flushing process.

The envelope 12-14 is deposited in a toilet, bottom portion first. The convergent shape of the pouch 10 and the non-obtrusive adhesive wafer 38 enable the envelope 12-14 to flow in streamlined fashion through the toilet passages and sewer pipes. It has been found that flushability of the pouch 10 is enhanced when the pouch has a 15° to 25° angle of convergence and the width and pouch height are in the size ranges previously specified.

The removed coupling ring can be separately discarded in a garbage container or reused on a replacement envelope 12-14 that has an adhesive wafer 38 covered by silicone release paper. The release paper is thus removed and the coupling 32 installed. The replacement pouch 10 can then be interlocked with the coupling 60 on the abdominal wall 13.

Some advantages of the present invention evident from the foregoing description include an ostomy pouch that has a molded plastic coupling ring that can be removed from the pouch envelope to facilitate flush disposal of the envelope in a water-saver toilet. Removal of the coupling ring is easily accomplished by peeling from the pouch wall. The removed coupling ring can either be reused or discarded. The pouch envelope can be supplied to the user without the coupling ring so as to permit reuse of a single coupling ring. The V-shaped profile of the pouch, the thin walled structure of the pouch envelope, and the thin gauge of the adhesive wafer on the pouch envelope and the predetermined size range of pouch height, top width and convergence angle ensure that the pouch structure itself will not constitute an obstacle to flushability of the pouch, even in low flush volume toilets. The pouch thus provides substantially risk-free flush disposal capability and eliminates the need to resort to garbage disposal of a used ostomy pouch.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A flushable ostomy pouch for holding body waste that passes through a stoma comprising, a) an envelope formed of flexible plastic sheet material defining a waste collection chamber for body waste that passes through a stoma, b) a waste inlet opening formed in said envelope for passage of waste material from said stoma into said collection chamber, c) flexible coupling means on said envelope around said waste inlet opening for positioning said waste inlet opening around a stoma, d) adhesive bonding means for adhesively and detachably bonding said coupling means to said envelope, whereby said coupling means is removable from said envelope to facilitate flush disposal of said envelope in a toilet, said adhesive bonding means having a predetermined bonding strength that permits said coupling means to be peeled as a unit from said envelope so as to be reusable or discardable; and e) means for facilitating removal of said coupling member from said envelope.

2. The ostomy pouch as claimed in claim 1 further comprising a carrier sleeve for receiving said envelope therein prior to flushing.

3. The ostomy pouch as claimed in claim 1 wherein said envelope has a top end portion, a bottom end portion opposite said top end portion, and opposite side edges extending between said top end portion and said bottom end portion, said side edge portions converging toward each other in a direction from said top end portion to said bottom end portion such that said envelope in plan view is substantially V-shaped.

4. The ostomy pouch as claimed in claim 1 wherein said coupling means includes a coupling member and means for securing said coupling member around a stoma in a fixed position.

5. The ostomy pouch as claimed in claim 4 wherein said coupling member is a molded annular plastic member formed with a coupling portion, whereby said coupling portion is interengagable with a complementary-shaped coupling portion provided around the stoma.

6. The ostomy pouch as claimed in claim 5 wherein said means for facilitating removal includes said annular plastic member having a peripheral edge portion that is formed to permit bending of said edge portion away from said envelope to initiate peeling of said annular plastic member from said envelope.

7. The ostomy pouch as claimed in claim 6 wherein said annular plastic member includes indicator means at said peripheral edge to indicate where the annular plastic member is to be initially peeled from said envelope.

8. The ostomy pouch as claimed in claim 7 wherein said indicator means is formed with a touch detector to permit touch detection of said initial peel section.

9. The ostomy pouch as claimed in claim 8 wherein said touch detector is a recess in said peripheral edge.

10. A flushable ostomy pouch for holding body waste that passes through a stoma comprising, a) an envelope formed of flexible plastic sheet material defining a waste collection chamber for body waste that passes through a stoma, b) a waste inlet opening formed in said envelope for passage of waste material from said stoma into said collection chamber, c) flexible mechanical coupling means on said envelope around said waste inlet opening for positioning said waste inlet opening around a stoma, d) adhesive bonding means for adhesively and detachably bonding said coupling means to said envelope, whereby said coupling means is removable from said envelope to facilitate flush disposal of said envelope in a toilet said adhesive bonding means having a predetermined bonding strength that permits said coupling means to be peeled as a unit from said envelope so as to be reusable or discardable, e) means for facilitating removal of said coupling member from said envelope; and f) said envelope having a top end portion, a bottom end portion opposite said top end portion, and opposite side edges extending between said top end portion and said bottom end portion, said side edge portions converging toward each other in a direction from said top end portion to said bottom end portion such that said envelope in plan view is substantially V-shaped with an angle of convergence in the range of approximately 15° to 25°.

11. The ostomy pouch as claimed in claim 10 wherein said coupling means includes a coupling member and means for securing said coupling member around a stoma in a fixed position, said coupling member being formed of a molded annular plastic with a coupling portion that interengages a complementary shaped coupling portion provided around a stoma.

12. A method for facilitating flush disposal of an ostomy pouch comprising, a) forming an envelope of flexible plastic sheet material with a waste inlet opening and a waste collection chamber, b) detachably adhesively bonding a flexible coupling member onto the envelope around the waste inlet opening to position the waste inlet opening around a stoma, c) including in the envelope-coupling member combination, means for facilitating peeling of the coupling member from the envelope, d) removing the flexible coupling member as a unit from the envelope for discarding or reusing when the envelope is ready for disposal by manipulating the means for facilitating peeling; and e) flushing the envelope down a toilet without the coupling member.

13. The method of claim 12 wherein the step of bonding includes joining the coupling member to the envelope by an adhesive tape that is joined to the envelope at a non-adhesive side and which holds the coupling member at the adhesive side.

14. The method of claim 12 wherein the step of removing the coupling member from the envelope includes the step of initiating removal at an initial peel section that is indicated with a touch detector.

15. The method of claim 12 wherein the step of forming includes forming the envelope in a V-shape.

16. The method of claim 12 further including the step of depositing the envelope in a carrier sleeve that becomes slippery upon immersion in water.

17. The method of claim 12 further including the step of severing the top portion of the envelope.

* * * * *